(12) United States Patent
Bimbo et al.

(10) Patent No.: US 6,551,270 B1
(45) Date of Patent: Apr. 22, 2003

(54) DUAL LUMEN ACCESS PORT

(75) Inventors: Frank Bimbo, Lawrenceville; Chad Garrish, Alto; Robert F. Leonard, Suwanee; Adrian C. Lock, Lawrenceville, all of GA (US)

(73) Assignee: Snowden Pencer, Inc., Tucker, GA (US)

( * ) Notice: Subject to any disclaimer, the term of this patent is extended or adjusted under 35 U.S.C. 154(b) by 76 days.

(21) Appl. No.: 09/651,191

(22) Filed: Aug. 30, 2000

(51) Int. Cl.[7] .............................................. A61M 11/00
(52) U.S. Cl. ................. 604/93.01; 604/99.03; 604/264; 604/167.03
(58) Field of Search ..................... 604/93.01, 99.03, 604/264, 27, 34, 167.02, 167.03, 236, 247, 284, 174; 606/167, 170, 1

(56) References Cited

U.S. PATENT DOCUMENTS

| | | | | |
|---|---|---|---|---|
| 3,777,757 A | * | 12/1973 | Gray et al. ............... | 604/99.03 |
| 5,071,405 A | * | 12/1991 | Pointek et al. ............... | 604/284 |
| 5,125,897 A | * | 6/1992 | Quinn et al. ............. | 604/99.03 |
| 5,183,471 A | | 2/1993 | Wilk | |
| 5,269,772 A | * | 12/1993 | Wilk ........................... | 604/284 |
| 5,569,205 A | | 10/1996 | Hart et al. | |
| 5,643,301 A | * | 7/1997 | Mollenauer ................. | 606/167 |
| 5,672,168 A | * | 9/1997 | de la Torre et al. ............. | 606/1 |
| 5,743,881 A | * | 4/1998 | Demco ................... | 604/167.02 |
| 5,803,921 A | * | 9/1998 | Bonadio ......................... | 606/1 |
| 5,857,999 A | * | 1/1999 | Quick et al. ................ | 604/264 |
| 6,066,112 A | * | 5/2000 | Quinn ..................... | 604/93.01 |
| 6,210,397 B1 | * | 4/2001 | Aboul-Hosn et al. ........ | 604/174 |

FOREIGN PATENT DOCUMENTS

| | | |
|---|---|---|
| EP | 0 646 358 A1 | 4/1995 |
| EP | 1 000 583 A1 | 5/2000 |
| FR | 2 710 270 A1 | 3/1995 |

OTHER PUBLICATIONS

INTERNATIONAL SEARCH REPORT, dated Feb. 20, 2002, for PCT Application No. PCT/US01/26353, 5 pps.

* cited by examiner

Primary Examiner—Teresa Walberg
Assistant Examiner—Fadi H. Dahbour
(74) Attorney, Agent, or Firm—Smith, Gambrell & Russell, LLP

(57) ABSTRACT

A port assembly adapted for insertion into the tissue of a patient during laparoscopic or endoscopic surgery wherein the port assembly includes an access port having a plurality of openings therein to allow for the insertion of multiple surgical instruments therethrough while maintaining a barrier to the flow of gas from the body cavity of the patient to the atmosphere. The access port is positioned in the housing of the port assembly and preferably includes two or more circular or semi-circularly shaped openings therein and a sealing member associated therewith to allow for the independent movement of the instruments therethrough.

4 Claims, 10 Drawing Sheets

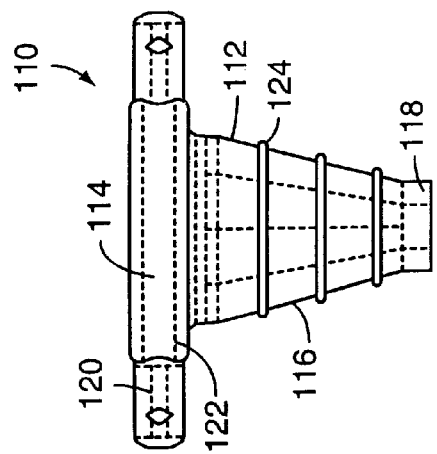
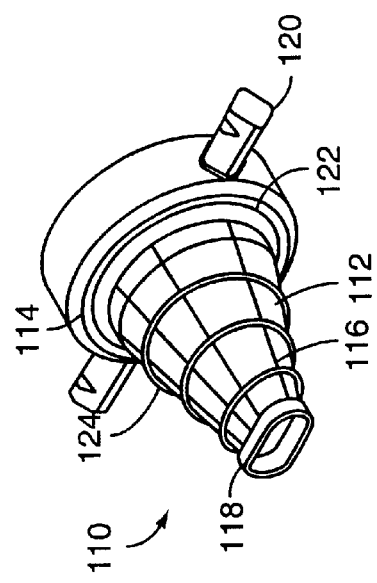
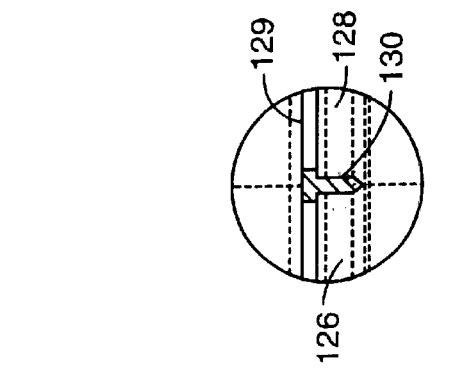
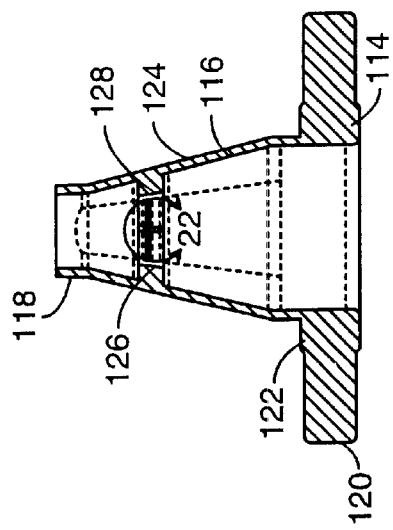
FIG. 19
FIG. 22
FIG. 21
FIG. 18
FIG. 20

DUAL LUMEN ACCESS PORT

FIELD OF THE INVENTION

This invention relates to a device for use in laparoscopic or other minimally invasive surgery and more particularly to an improved access port for use in laparoscopic surgery.

BACKGROUND OF THE INVENTION

In laparoscopic procedures, surgery is performed in the interior of the abdomen through a small incision. In endoscopic procedures, surgery is performed in any small area of the body through narrow or small diameter tubes inserted through a small entrance incision in the skin. Laparoscopic and endoscopic procedures generally require that any instrumentation that is inserted into the body be of minimal diameter and preferably be sealed with respect to the tissue of the patient to retain the gas that is added to insufflate the area of the surgery to create a working space for the surgeon. Moreover, laparoscopic and endoscopic procedures often require the surgeon to act on organs, tissues and vessels that are far removed from the incision, thereby requiring that any instruments used in such procedures be relatively long and of a small diameter. Additionally, because many of these procedures are performed on the abdomen or other areas that are visible to other people, there is a desire to use as few incisions as possible and to minimize the size and location of any resulting scars.

For such procedures, the introduction of a tube into the anatomical cavity, such as the abdomen, is usually accomplished through the use of a trocar assembly consisting of a port assembly and a trocar. The port assembly generally consists of a tubular port and a sealing member. Since the port assembly is in direct communication with the abdominal cavity of the patient, the sealing member must maintain a tight seal between the abdominal cavity and the atmosphere throughout the procedure, including as each instrument is inserted and manipulated therethrough. Surgical procedures in the abdominal cavity of the body, often require the use of insufflating gases to raise the cavity wall away from vital organs to form the working space. Therefore, a Veres needle is often used to initially pierce the abdominal wall and then introduce the gas into the abdominal cavity. Thereafter a pointed trocar is inserted into the port assembly and is used to pierce the abdominal wall. The gas raises the inner wall surface away from the vital organs thereby avoiding unnecessary and potentially dangerous contact with the organs as the instruments are inserted into the port assembly. Following removal of the trocar, laparoscopic or endoscopic instruments may then be inserted through the port assembly to perform surgery within the body cavity.

In view of the need to prevent leakage of the insufflation gas from the cavity, the port assembly is typically provided with a valve or seal assembly to permit introduction of the trocar and surgical instrument therethrough while minimizing communication between the abdominal cavity and the atmosphere. In this regard, there have been many attempts to provide a secure seal as part of the port assembly to allow for the secure insertion of a single instrument through the port. It frequently occurs during surgery that an additional instrument is temporarily required or desirable. Inserting this extra instrument typically involves creating an additional incision with a trocar. It is preferable that the number of incisions be minimized and that all of the required instruments remain in the cavity. Although larger port assemblies have been manufactured that may allow temporary access for multiple instruments through a single port, the seal may be lost and the insufflation gas will pass through leaks in the seal because the seals are designed for sealing around a single instrument. Additionally, as the second instrument is manipulated around the first instrument, the sealing member is unable to seal around the shaft of both instruments even if the surgeon is able to insert both instruments through the common port assembly. Therefore, the wall of the cavity will collapse and the likelihood of accidentally contacting tissue or organs with one or more of the instruments is increased.

At least one attempt has been made to allow the use of multiple instruments through a single port assembly. An example of this approach is disclosed in U.S. Pat. No. 5,395,367 granted to Wilk. In this disclosure, a device having multiple distal end effectors and multiple proximal actuators is disclosed. The device disclosed in the Wilk patent includes an elongate rigid sleeve having a pair of instruments movable therein. The rigid sleeve is inserted into a standard trocar sleeve or port assembly. The locking elements of this device are used to fix the position of the instruments relative to each other and limit the relative movement of the instruments through the rigid sleeve. Despite the availability of a plurality of end effectors through the common port assembly, this device still requires the use of a unique and relatively complicated instrument to perform multiple manipulations through the common port. Additionally, the instruments used with this device require that the end effectors be located adjacent to each other and cannot be oriented at different angles with respect to each other. Therefore, there is a need to provide a port assembly that allows the surgeon to use multiple instruments through a common incision. It is further desirable to allow the surgeon to use the instruments that they are familiar with and allow them to use a specialized port assembly that may be used with one instrument or a second instrument if desired without changing their technique.

SUMMARY OF THE INVENTION

An object of the present invention is to provide an improved port assembly and an associated method for facilitating laparoscopic or endoscopic surgery.

Another object of the present invention is to provide a port assembly that facilitates the utilization of an increased number of instruments without changing the technique of the surgeon or the number of incisions required to accomplish the desired procedure.

Yet another object of the present invention is to provide a port assembly that is sufficiently versatile to allow the surgeon to use the port assembly with either a single instrument or to add a second instrument through the same port.

Yet another object of the present invention is to provide a port assembly that is sufficiently versatile to allow independent movement and use of two instruments through the same port assembly.

Yet another object of the present invention is to provide a port assembly that includes floating valves to allow independent movement and use of two instruments through the same port assembly.

A preferred form of the present invention includes a port assembly that permits introduction of one or more elongate objects such as laparoscopic or endoscopic instruments therethrough. These instruments typically have a circular cross section and are inserted through the port assembly and into the body of the patient to perform the desired manipulation, cutting, suturing or removal desired by the surgeon. The port assembly of the present invention preferably includes a pair of floating valves or seals that allows independent dual access through the access opening of the port while maintaining a seal between the cavity and the atmosphere.

Additionally, one form of the present invention includes one or more valve bodies formed of a resilient material that will cause the flexible material surrounding the access opening to surround and resiliently engage the instrument or instruments in a substantially gas tight manner. The access opening may further include one or more slit valves or flexible flap members that are normally closed to further seal the port assembly. In a further embodiment, the access openings extend from the body of the port assembly such that individual sealing members may be used and opened by the individual instruments as the access is needed or desired. In this embodiment, the access openings open into a larger body area which is positioned in the tissue of the patient so that the separate manipulation of the instruments may be accomplished without affecting or compromising the substantially gas tight seal.

In yet another embodiment, the port assembly is preferably a rigid or semi-rigid member having a pair of sealing members therein. The sealing members may be individual slit or flap members such that the substantially fluid tight seal is formed around the individual instruments to allow individual manipulation of each instrument as desired.

The port assemblies of the present invention are preferably generally conically shaped and may be tapered from top to bottom to assist the surgeon with the insertion of the port assembly into the tissue of the patient. Alternately, the port assembly may be tapered inwardly towards the middle section with the distal and proximal sections being larger than the middle section to assist in retaining the tissue therebetween. In the first generally conical shape, the port assembly may also include an enlarged lip area to provide a stop surface for the port assembly such that the surgeon inserts the port assembly into the tissue of the patient up to the bottom surface of the lip member. Additionally, a smaller lip area may be located on the distal end portion to assist in retaining the port assembly in the tissue of the patient and contributing to the maintenance of the substantially gas tight seal.

An advantage of the present invention is that the port assembly allows the surgeon to use one or more instruments through the same incision while maintaining the substantially gas tight seal to maintain the insufflation of the desired cavity.

Another advantage of the present invention is that the surgeon may use straight and/or curved instruments with the present invention to obtain as much access as possible through a single incision while facilitating the performance of the surgical procedure by allowing the shaft of an additional instrument to be inserted adjacent to a first instrument on an as needed basis.

Yet another advantage of the present invention is that the port assembly provides the surgeon with the ability to separately manipulate the instruments through the separate access openings in the same port assembly to maximize the surgeon's ability to manipulate and grasp the desired tissue.

A further advantage of the present invention is that the port assembly may be used in place of currently available port assemblies such that the port assembly of the present invention allows the surgeon to use their current techniques while allowing additional access in the event that an additional instrument is needed without requiring an additional incision or special instrumentation.

BRIEF DESCRIPTION OF THE DRAWINGS

The foregoing features and benefits of the present invention will become more readily apparent and will be further understood by referring to the following drawings and detailed description of the preferred embodiments of the present invention set forth below wherein like numbers are used to describe like elements. The present invention contemplates introduction into the body of a patient all types of surgical instruments including, but not limited, clip appliers, lasers, endoscopes or other visual aids, graspers, scissors, tubes, or cautery devices. All of these types of devices are generically referred to herein as instruments.

FIG. 18 is a perspective view of an alternate embodiment of the present invention;

FIG. 19 is a side perspective view of the embodiment shown in FIG. 18;

FIG. 20 is a bottom view of the embodiment shown in FIG. 18;

FIG. 21 is a side cross sectional view of the embodiment of FIG. 18 taken generally along lines 21—21 of FIG. 19; and FIG. 22 is an enlarged cross sectional view of the access opening of the embodiment of FIG. 18.

DETAILED DESCRIPTION OF THE PREFERRED EMBODIMENTS OF THE PRESENT INVENTION

Figure 1:
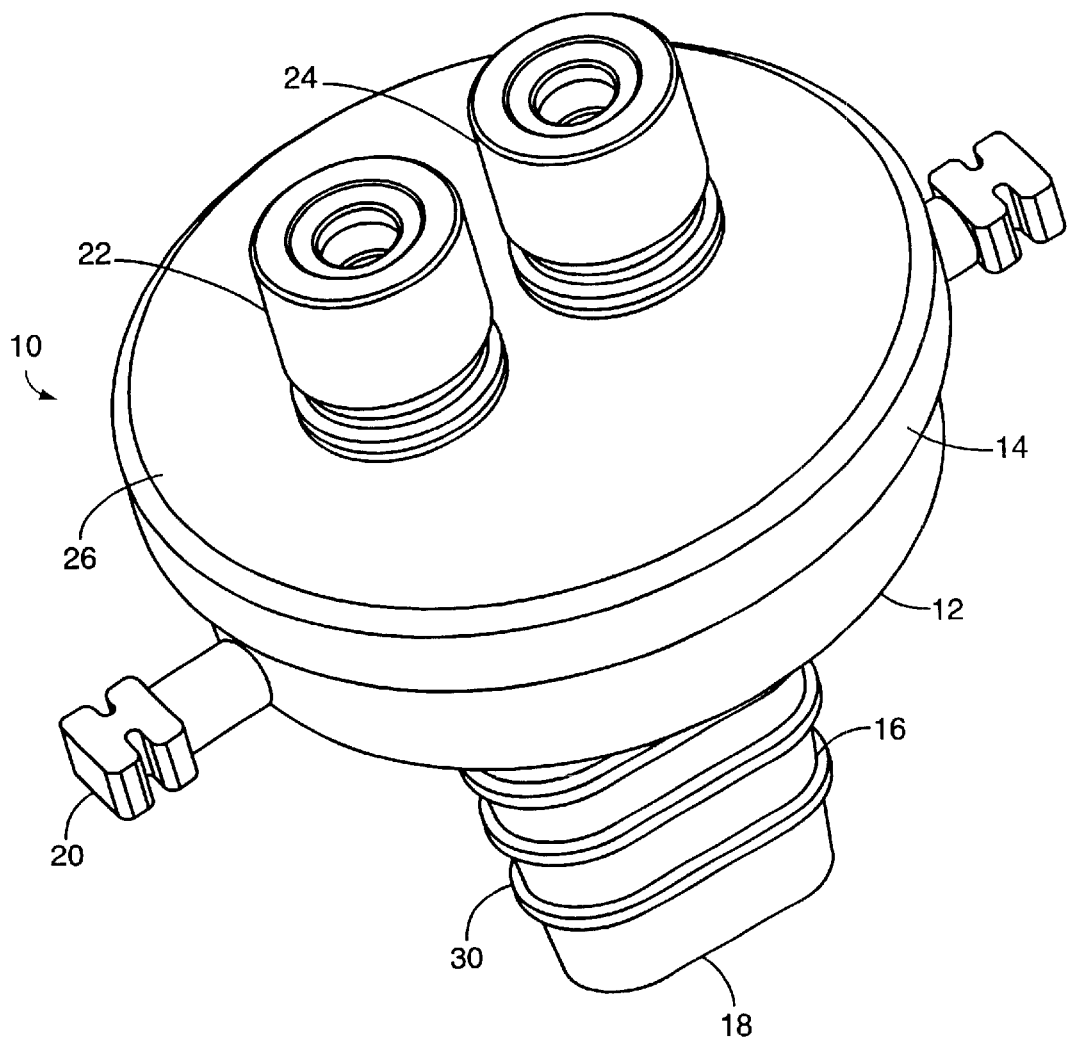
FIG. 1 is a top perspective view of a preferred embodiment of the present invention.
Figure 2:
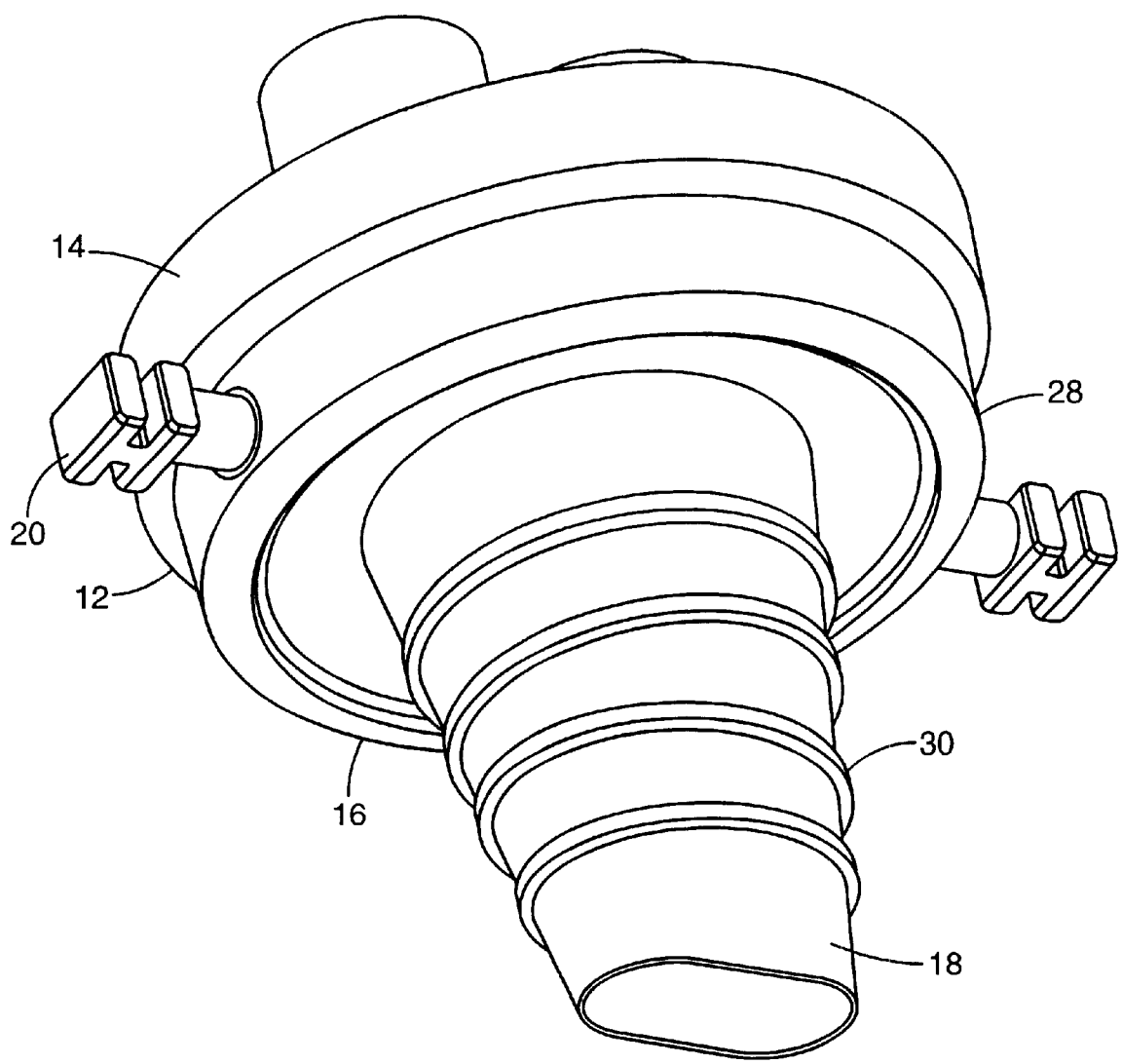
FIG. 2 is a bottom perspective view of the embodiment shown in FIG. 1.
Figure 3:
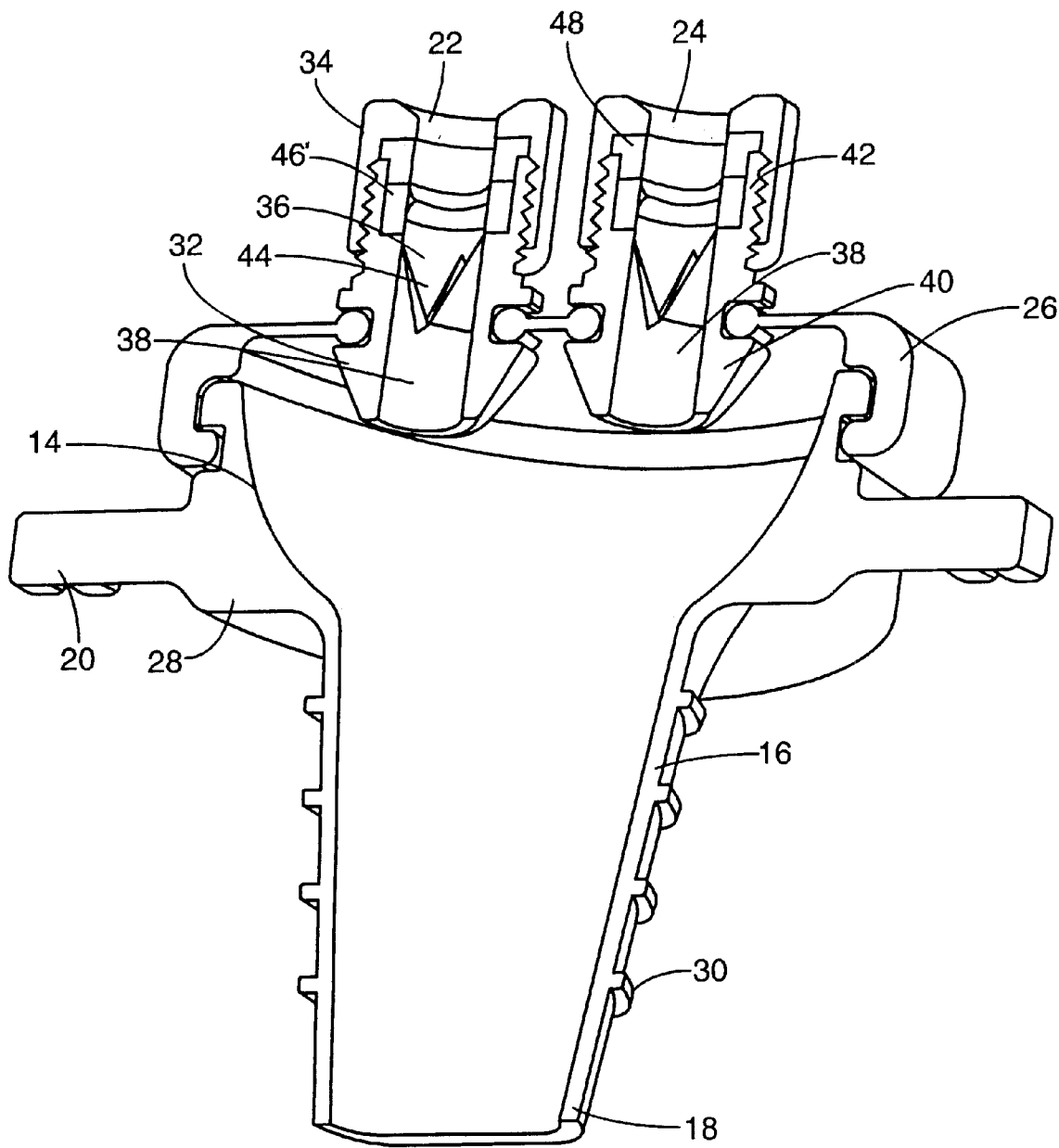
FIG. 3 is a cross sectional view of the embodiment of FIG. 1 taken generally along lines 3—3 of FIG. 1.
Figure 4:
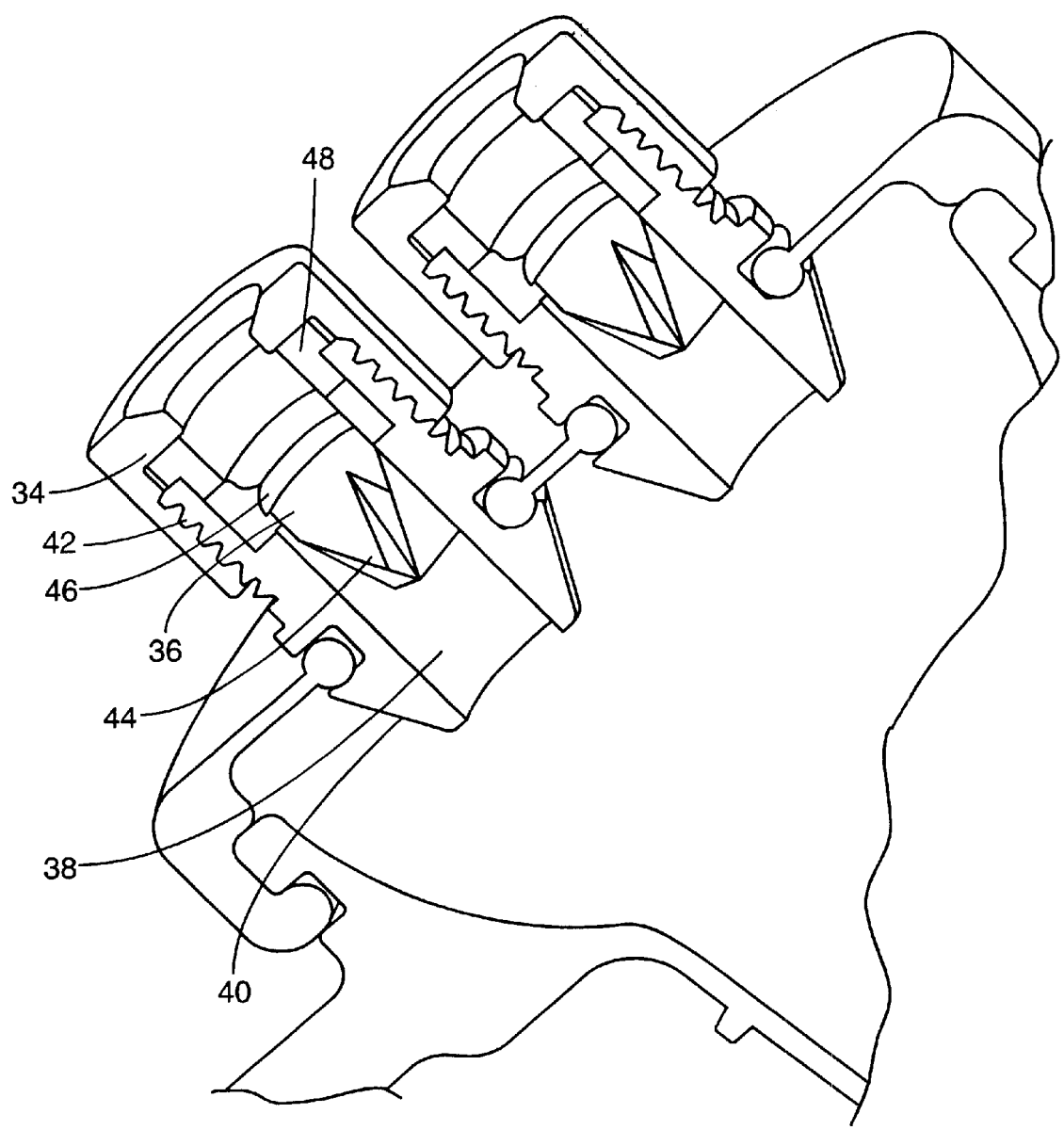
FIG. 4 is an enlarged cross sectional view of the access opening of the embodiment of FIG. 1 similar to the view shown in FIG. 3.

The port assembly of the present invention is preferably a flexible or semi-rigid member having an outer housing with an expanded upper or proximal section, a middle section and a distal section. The overall shape of the port assembly is generally tapered and chosen so that the elasticity of the skin of the patient assists in the retention of the port assembly in the incision formed in the body of the patient. The diameter of the proximal section is sufficiently enlarged to assist the surgeon in inserting the instruments through the port assembly. Additionally, the use of the larger diameter proximal section allows the surgeon to separate the handle portions of the multiple instruments from each other so that they do not interfere with each other and are easily identified as far as the end effector that each handle operates. Additionally, if curved instruments are used, the handles are easily separated and may be separately manipulated to perform the desired procedure and the operative area that may be reached by each instrument is increased without requiring instruments that are unique to the desired procedure. As described more fully below, the present invention preferably includes a plurality of spaced apart valve members in each port assembly.

The general insertion of the port assembly is accomplished by stretching the tissue of the patient as the port assembly is inserted in to the incision and then allowing the normal elasticity of the tissue to contract along the outer housing adjacent to the middle section. As described more fully below, this contraction of the tissue along the middle section of the port assembly assists in maintaining the substantially gas tight seal along between the body cavity and the atmosphere along the housing of the port assembly. The port assembly of this embodiment may be made of a non-reactive and resilient material such as a rubber or similar elastomeric material.

In the embodiment shown generally in FIGS. 1–4, the port assembly 10 is preferably a flexible or semi-rigid member having an outer housing 12 with an expanded upper or proximal section 14, a middle section 16 and a distal section 18. The proximal section 14 includes a pair of post members 20 extending laterally from the outer housing 12. Additionally, the proximal section 14 includes a pair of access openings, 22 and 24, of this embodiment are positioned on the top surface 26 of the proximal section 14 and preferably extend upwardly therefrom. The outer circumference of the proximal section 14 adjacent to the middle section 16 is enlarged to form a stop surface 28 distally of the post members 20 so that the user may push or twist the port assembly 10 into the hole in tissue of the patient until the tissue is snug on one of the annular or threaded ridges. As this occurs, the tissue is stretched and contacts the outer surface of the middle section 16 of the outer housing 12 to form a substantially tight gas seal therebetween. The middle section 16 also preferably includes a plurality of circumferential rib members 30 on the outer surface thereof. These rib members 30 contact the stretched tissue surrounding the port assembly to provide a secure seal therebetween and minimize the longitudinal movement of the port assembly 10 in the incision. The distal section 18 of this embodiment is preferably semi rigid and generally has an oblong shaped cross section. The distal section 18 is preferably oriented generally perpendicular to the top surface of the port assembly and is oriented to allow the instruments to extend beneath this opening and deform this section of the port assembly without jeopardizing the seal between the cavity and the atmosphere.

The access openings, 22 and 24, of this embodiment are positioned on the top surface of the proximal section 14 and preferably extend upwardly therefrom. The top surface 26 of the port assembly 10 is flexible and may be readily deformed without jeopardizing the seal between the cavity and the atmosphere. Additionally, the access openings 22 and 24 of this embodiment are preferably formed as separate components from the top surface 26 and the proximal section 14. Each access opening preferably includes a tubular body section 32, a cap member 34 and a valve member 36. As shown, the interior of the tubular body 32 includes a central opening 38 extending therethrough. The exterior of the tubular body 32 preferably includes a distal rib surface 40 and a proximal threaded surface 42. The valve member 36 preferably includes one or more flap members 44 and even more preferably includes a duck bill type of valve member wherein a plurality of flap members are biased to press against each other to seal the central opening 38. The flap members 44 assist in retaining the insufflation gas within the cavity by forming a seal against each other and/or the interior of the body section to seal the inner surface of the body tissue from the atmosphere prior to and once the port assembly is inserted into the patient. The valve member 36 preferably also includes an upper lip member 46. This lip member 46 extends inwardly into the central opening 38.

The cap member 34 of each of the access openings, 22 and 24, is threadedly received on the tubular body 32 of the access openings. The cap member 34 of this embodiment assists in retaining the valve member 36 in the interior of the tubular body 32. In an alternate embodiment, the resistance to movement of the instrument through the access port may be adjusted by rotating the cap member in a clockwise or counterclockwise manner. For example, if the cap member 34 is rotated in a clockwise manner, the top portion of the cap member 34 compresses a washer member 48 located on the top portion of the valve member. This compression causes the upper lip member 46 to deform and extend further into the central opening 38. Therefore, when an instrument is positioned in the access port, rotation of the cap member 34 in a clockwise direction will cause the washer member 48 to deform and press against the upper lip member 46 which then presses against the outer surface of the instrument. If the surgeon decides to remove the instrument form the access port, the cap member 34 may be rotated in a counterclockwise direction and the upper lip member 46 will return to the uncompressed position wherein there is less or no contact with the outer surface of the instrument. As described herein, each access port is preferably individually adjustable so that the surgeon may move or retain the instruments independently from each other as desired. Additionally, the flexibility of the top surface 26 also increases the user's ability to individually manipulate the instruments through each access opening, 22 and 24.

The inner surface of the housing 12 is generally open and conforms to the outer surface of the housing. This allows the instruments to be manipulated as much as possible while minimizing the restriction of movement caused by the use of the port assembly 10. In the present embodiment, the valve member 36 restricts movement of the instrument by providing a pivot point along the proximal portion of the housing. Therefore, as the surgeon moves the instrument laterally, the instrument pivots along the valve member 36 and the portion of the instrument that is distal to the valve member 36 is allowed to move laterally, until it contacts the sidewalls of the distal section 18. Additionally, because the distal section 18 is preferably deformable, the instruments may continue to move laterally with respect to each other by deforming the distal section of the housing.

Figure 5:
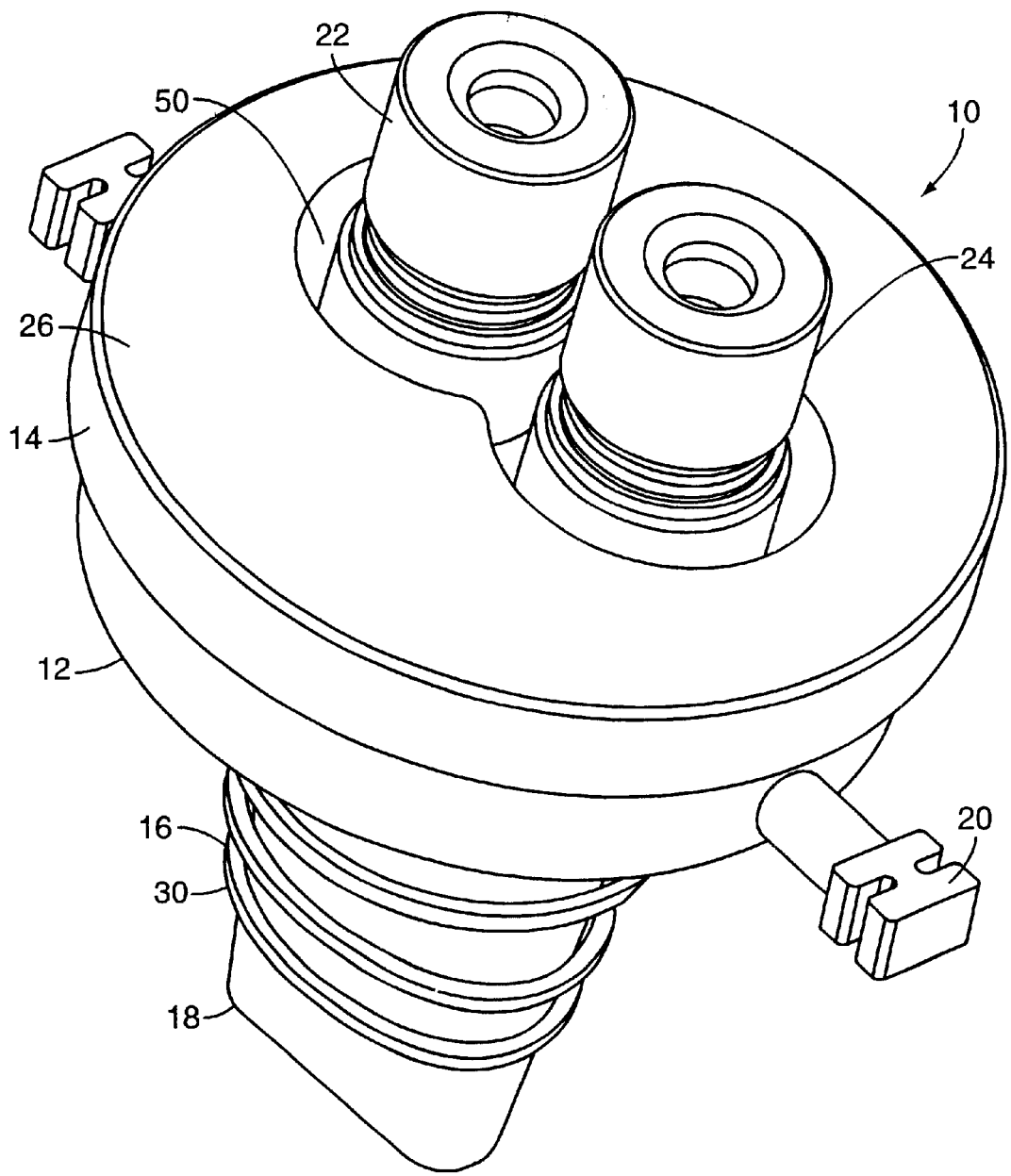
FIG. 5 is a top perspective view of a further preferred embodiment of the present invention.
Figure 6:
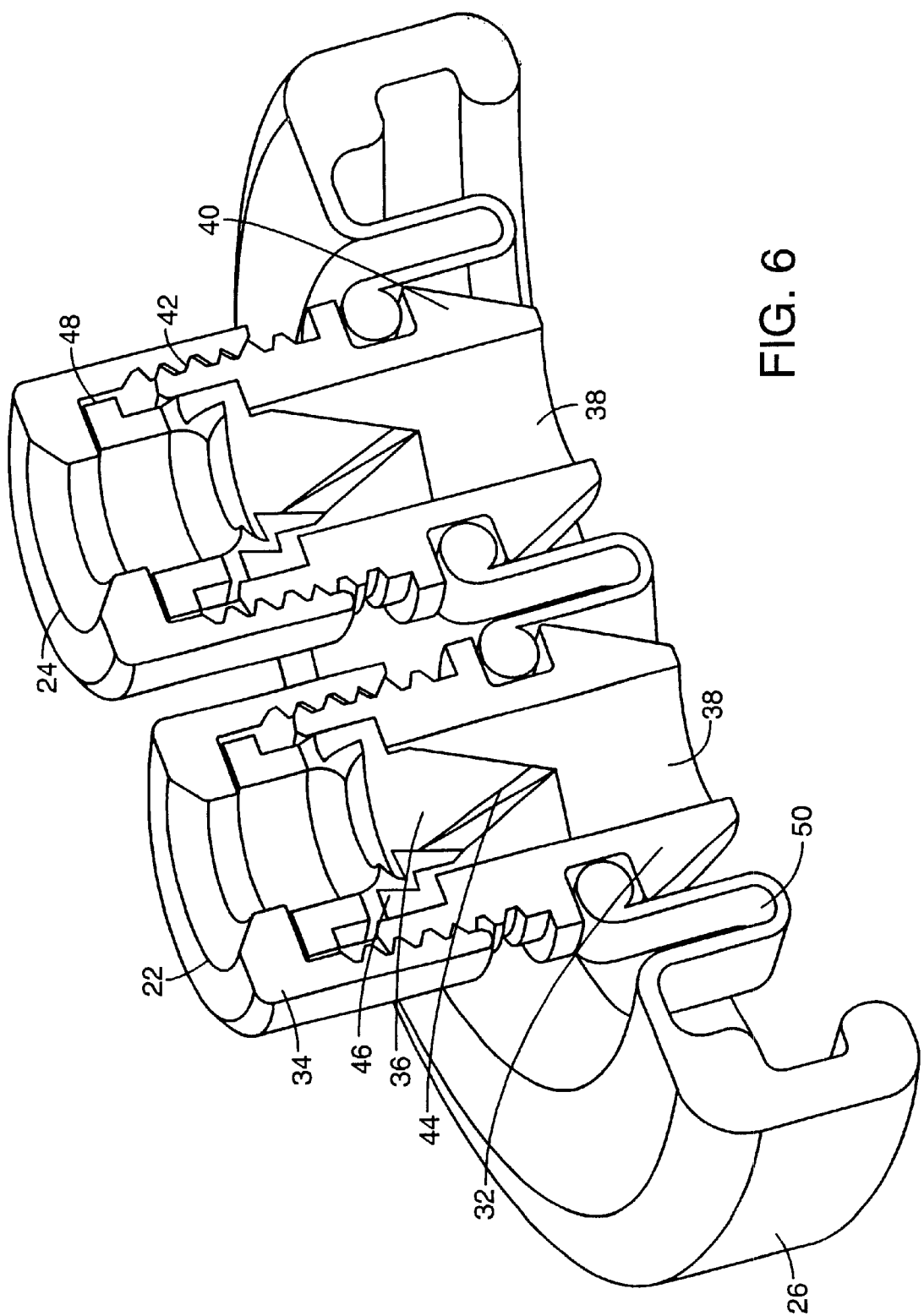
FIG. 6 is a cross sectional view of the embodiment of FIG. 5 taken generally along lines 6—6 of FIG. 5.
Figure 7:
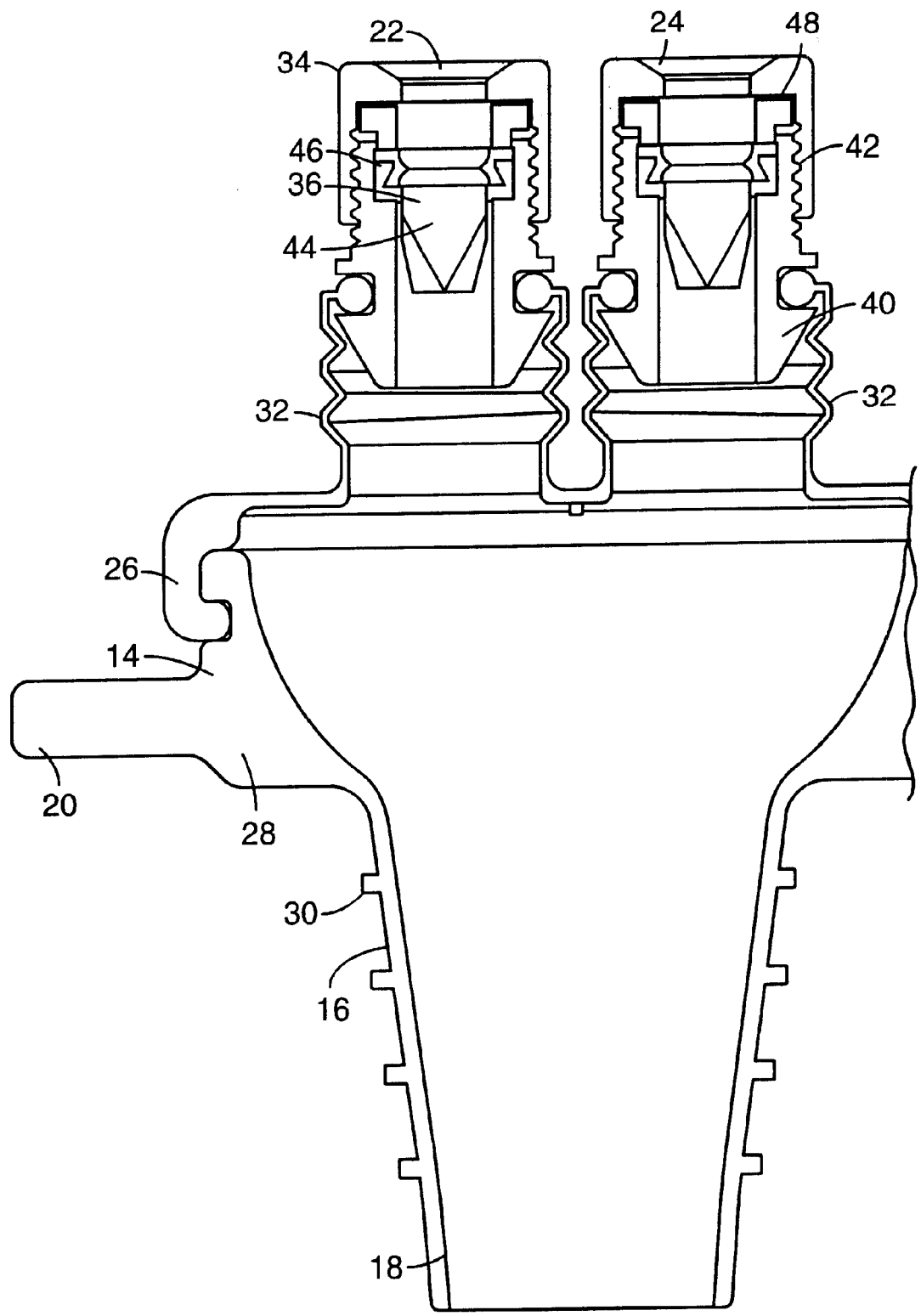
FIG. 7 is a cross sectional view of a further preferred embodiment of the present invention taken generally along similar lines as the embodiment shown in FIG. 6.
Figure 8:
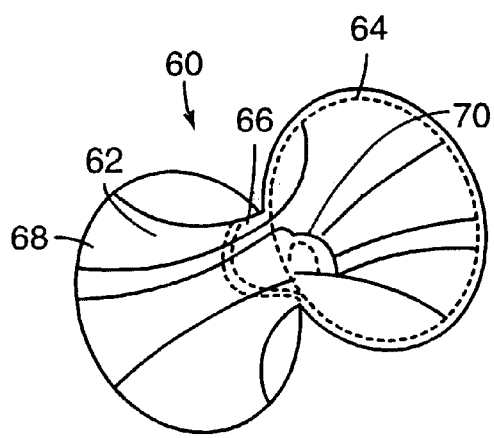
FIG. 8 is a perspective view of a further preferred embodiment of the present invention.
Figure 9:
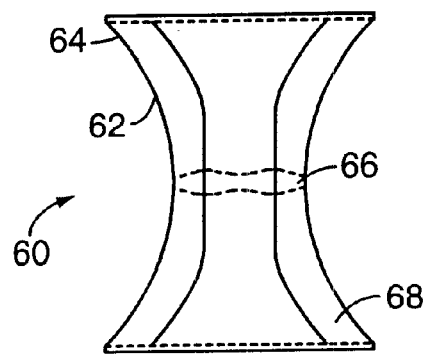
FIG. 9 is a side view of the embodiment of the present invention shown in FIG. 8.
Figure 10:
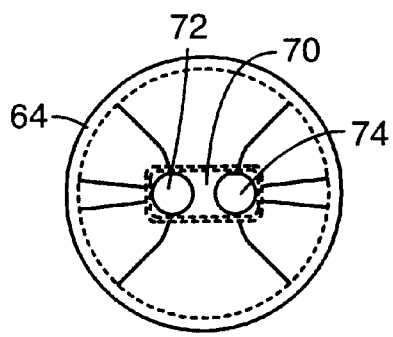
FIG. 10 is a top view of the embodiment of the present invention shown in FIG. 8.
Figure 11:
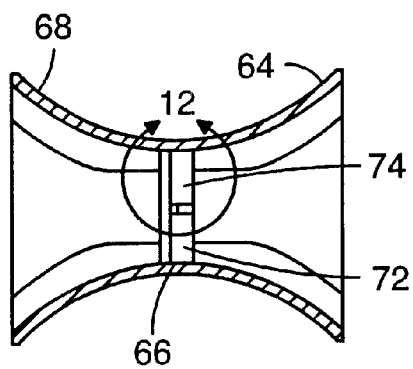
FIG. 11 is a side cross sectional view taken generally along lines 11—11 of FIG. 9.
Figure 12:
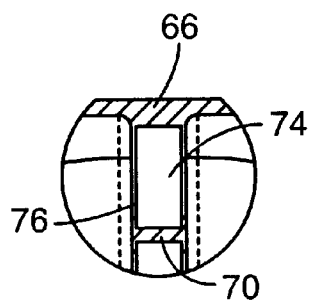
FIG. 12 is an enlarged cross sectional view of the access opening of the embodiment of FIG. 8.
Figure 14:
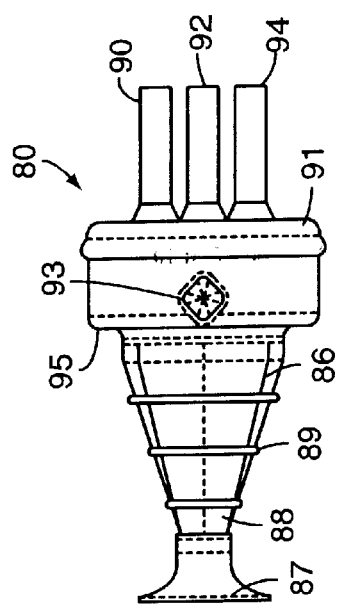
FIG. 14 is a side perspective view of the embodiment shown in FIG. 13.
Figure 17:
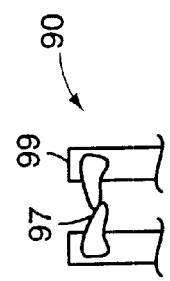
FIG. 17 is an enlarged cross sectional view of the access opening of the embodiment of FIG. 13.
Figure 16:
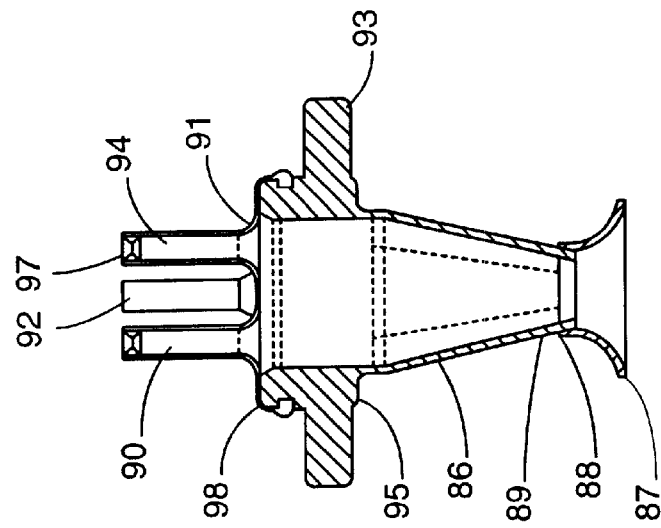
FIG. 16 is a side cross sectional view of the embodiment of FIG. 13 taken generally along lines 16—16 of FIG. 14.

FIGS. 5–7 illustrate further preferred forms of a port assembly 10 of the present invention wherein like numbers are applied to like elements. For the sake of brevity, many of the elements described above are not repeated herein. The port assembly 10 of these embodiment are preferably a flexible or semi-rigid member having an outer housing 12 with an expanded upper or proximal section 14, a reduced diameter middle section 16 and further tapering lower or distal section 18. The overall shape of the port assembly 10 is chosen so that the elasticity of the skin of the patient assists in the retention of the port assembly 10 in the incision formed in the body of the patient. The diameter of the proximal section 14 is sufficiently enlarged to assist the surgeon in inserting the instruments through the port assembly. Additionally, the use of the larger diameter proximal section 14 allows the surgeon to separate the handle portions of the multiple instruments from each other so that they do not interfere with each other and are easily identified as far as the end effector that each handle operates. Additionally, if curved instruments are used, the handles are easily separated and manipulated to perform the desired procedure and the operative area that may be reached by each instrument is increased without requiring instruments that are unique to the desired procedure.

The access openings, 22 and 24, of the embodiment shown in FIGS. 5 and 6 are positioned on the top surface of the proximal section 14 and preferably extend upwardly therefrom. In this embodiment, the top surface 26 of the port assembly 10 includes a further recess 50 that surrounds and separates the access openings 22 and 24. The use of the additional recess 50, increases the flexibility of the top surface and also allows the access ports to be further depressed into the housing and stretched with respect to each other to increase the user's ability to manipulate the desired instruments. In the embodiment shown in FIG. 7, the access openings, 22 and 24, each also include a tubular body portion 52 that is generally bellows shaped to further increase the flexibility and movement of the access openings relative to the proximal section 14 of the port assembly. Additionally, the access openings 22 and 24 of these embodiments are preferably formed as separate components from the top surface 26 and the proximal section 14. Each access opening of these embodiments preferably include a tubular body section 32, a cap member 34 and a valve member 36. As shown, the interior of the tubular body 32 includes a central opening 38 extending therethrough. The valve member 36 preferably includes one or more slit or flap members 44 and even more preferably includes a valve member wherein a plurality of slit or flap members are biased to press against each other to seal the central opening 38.

FIGS. 8–12 are illustrative of a further embodiment of the present invention. This embodiment includes a port assembly 60 having an outer housing 62 with an enlarged upper or proximal section 64, a reduced diameter middle section 66 and an expanded or lower distal section 68. The overall shape of the port assembly 60 of this embodiment is chosen so that the elasticity of the skin of the patient assists in the retention of the port assembly 60 in the body of the patient. The diameter of the proximal section 64 is sufficiently large to assist the surgeon in inserting the instruments through the port assembly 60. The size of the proximal section 64 also assists in the independent manipulation of the instruments through the port assembly 60 by providing a large diameter area for the manipulation of the handles and shafts of the instruments. The diameter of the distal section is also sufficiently large to assist the surgeon in sealing the port assembly 60 against the skin of the patient and retaining the port assembly 60 in the skin of the patient while allowing the distal portion of the instruments to be independently manipulated.

In this embodiment, the interior of the middle section 66 includes an access opening 70 having a pair of spaced-apart openings extending therethrough. As shown, the first opening 72 and second opening 74 are preferably circular and extend through the middle section 66. The access opening 70 is preferably formed of a resilient material that surrounds the first opening 72 and second opening 74 and which allows the openings to contact and independently close around the diameter of an instrument. Although the first and second openings are shown herein as separate circular openings, it is anticipated that the openings may also be formed as a double "D" shaped configuration in the event that it is desirable to further minimize the outer diameter of the middle section of the port assembly by using a circular or generally oval shape for the overall shape of the access opening 70.

The first opening 72 and the second opening 74 are preferably closed by one or more slit or flap members 76 whether the middle section 66 of the port assembly 10 is compressed or uncompressed. The flap member or members 76 extend across the first opening 72 and the second opening 74 as separate members on the side of the port assembly 60 nearest to the distal section 68 of the port assembly 60 so that when the port assembly 60 is in use, the pressure of the insufflation gas will cause the flap member 76 to press against the respective first or second opening and prevent the flow of gas therethrough. Additionally, because the first and second openings are formed of resilient material and are independently movable form across the first and second opening, the instruments may easily pass therethrough while maintaining the seal around the diameter of the instrument.

The preferred embodiments shown in FIGS. 13–17, 18–15 and 16–19 are more conventionally shaped port assemblies wherein the diameter of the proximal section 84 and 114, respectively, is larger than the diameter of the distal section 88 and 118, respectively. As shown in FIGS. 13–17, an alternate preferred embodiment of the present invention is a port assembly 80 that includes the outer housing 82 having a proximal section 48, a middle section 86 and a distal section 88. The proximal section 84 preferably includes a plurality of upstanding access ports 90, 92 and 94, thereon.

Each of the access ports 90, 92 and 94 include a sealing member 96 thereon that is spaced apart from the top surface 91 of the proximal section 84 to provide a seal or valve member thereon that substantially prevents the flow of gas therethrough while allowing the instruments to be individually inserted and manipulated therethrough. Each sealing member 96 preferably includes a slit or a pair of flexible valve or lip members 97 that are positioned along a ridge surface 99 formed at the top of the access ports 90, 92 and 94. The lip members 97 are configured so that the pressure from the insufflation gas causes the lip members 97 to press against each other and against the ridge surface to substantially retain the insufflation gas in the cavity of the patient. The access ports are preferably molded or formed separately from a resilient material and are attached to the outer housing 82 of the port assembly by conventional means. This may include a frictional fit utilizing the circumferential groove 98 shown in FIG. 13 wherein the member forming the access ports and top surface 91 is stretched around the housing and the member is stretched to fit in the circumferential groove 98 or the use of adhesives or similar bonding materials.

As shown, the preferred form of this embodiment includes a pair of handle members 93 that extend laterally outwardly from the proximal section 84 of the outer housing 82. This configuration allows the user to grasp the handle members 93 and twist the port assembly 80 as the port assembly 80 is inserted into the tissue of the patient. The distal surface of the handle members 93 also preferably extends outwardly from the proximal section 84 of the outer housing 82 to form a stop surface 95 thereon to limit the inward insertion of the port assembly 80 into the tissue of the patient.

The middle section 86 of the outer housing 82 preferably tapers inwardly from the handle members 93 and includes a plurality of circumferential rib members 89 to minimize the movement of the tissue of the patient when the port assembly 80 is inserted into the patient. The middle section 86 engages the adjacent tissue as the tissue contracts around the middle section 86 of the outer housing 82. In this embodiment, the distal section 88 includes an enlarged lip surface 87 that extends outwardly from the smaller diameter middle section 86. The lip surface 87 preferably has greater flexibility than the flexibility of the remainder of the outer housing 82 so that it may be readily manipulated for insertion into the tissue of the patient and to allow the instruments to stretch or deform this portion of the port assembly as the surgeon is performing the procedure.

Figure 13:
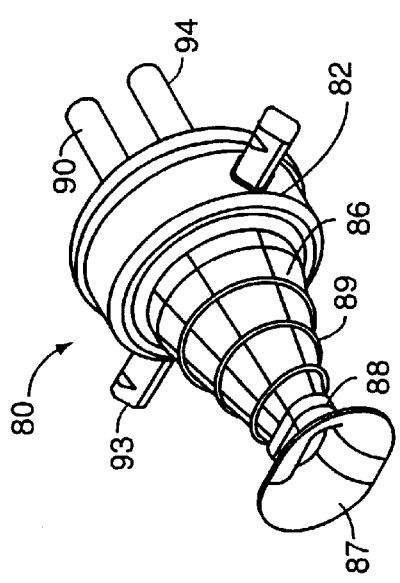
FIG. 13 is a perspective view of an alternate embodiment of the present invention.
Figure 15:
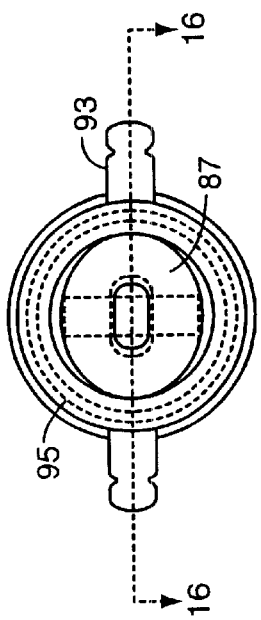
FIG. 15 is a bottom view of the embodiment shown in FIG. 13.

In this embodiment, the access openings 90, 92 and 94 are positioned in a spaced apart relationship with the proximal section 84, the user may stretch or deform this portion of the port assembly 80 without jeopardizing the seal between the cavity and the atmosphere. Additionally, the use of the lip surface 87 assists in retaining the insufflation gas within the cavity by forming a seal against the inner surface of the body tissue once the port assembly 80 is inserted into the patient. As shown in FIG. 13, the inner surface of the housing 82 generally conforms to the outer surface of the housing so that the instruments may be manipulated as much as possible with respect to each other and the port assembly 80 while minimizing any restriction of movement caused by the use of the port assembly.

FIGS. 18–22 illustrate a further preferred form of the present invention. The port assembly 10 of this embodiment preferably includes a housing 112 having a proximal section 114, a tapered middle section 116 and a smaller and generally oblong shaped distal section 118. In this embodiment, the proximal section 114 includes a pair of laterally extending handle members 120 along the proximal surface thereof. The outer circumference of the proximal section 114 is enlarged to form a stop surface 122 distally of the handle members 120 so that the user may grasp the handle members 120 and twist the port assembly 110 into the tissue of the patient until the tissue contacts the stop surface 122 of the proximal section 114. As this occurs, the tissue is stretched and contacts the outer surface of the middle section 116 of the housing 112 to form a substantially tight gas seal therebetween. The middle section 116 preferably includes a plurality of circumferential rib members 124 on the outer surface thereof These rib members 124 contact the stretched tissue surrounding the port assembly 110 to provide a secure seal and minimize the movement therebetween. The distal section 118 of this embodiment is preferably a flexible and generally oblong shaped member. The distal section 118 is preferably oriented generally perpendicular to the top surface of the port assembly 110 and is oriented to allow the instruments to deform this section of the port assembly without jeopardizing the seal between the cavity and the atmosphere.

As shown in FIG. 21, the access ports 126 and 128 of this embodiment are preferably located along the interior of the middle section 116 and spaced apart a short distance from the distal section 118. The access ports 126 and 128 include a plurality of flexible valve or lip members 129 thereon near the distal surface thereof to provide a seal that substantially prevents the flow of gas therethrough while allowing the instruments to be individually inserted and manipulated therethrough. Each lip member 129 is preferably configured so that the pressure from the insufflation gas causes the lip members 129 to press against each other and against a ridge surface 130 of the access ports 126 and 128 to substantially retain the insufflation gas in the cavity of the patient. The access ports of this embodiment are preferably molded as part of the housing of the port assembly or they may be formed separately from a resilient material and attached to the housing of the port assembly by conventional means. This may include a frictional fit or the use of adhesives or similar bonding materials.

In this embodiment, the lip members 129 form the sole sealing area between the open proximal section 114 and the open distal section 118 of the port assembly 110. This arrangement allows the instruments to be separately manipulated along a single pivot area through the access ports, 126 and 128 while the insufflation seal is maintained by the lip members 129.

In each of the above-described embodiments, the access ports are at various positions in the housing of the port assembly. The difference in location of the access ports affects the user's ability to manipulate the instruments through the port assembly by changing what generally becomes a hinge or pivot point during the procedure because the valve member is typically the narrowest location for the manipulation of the instruments. Therefore, when the access port is located along the proximal section, the housing between the access port and a restriction forms the hinge point. When the valve member is located at the middle section, the hinge point is generally along the middle of the housing at the narrowest point of the housing. When the access point is located distally of the middle section, the hinge point is moved distally to a location between the middle section of the housing and the distal section of the housing.

Another feature of the present invention is that the hinge or pivot location of the instruments may be positioned at different locations relative to the skin surface and peritoneum of the patient. For example, in the embodiments where the access ports are positioned above or adjacent to the proximal section, the hinge or pivot location of the instruments are located above the tissue surface of the patient to provide a floating valve type of configuration. This feature is further enhanced in the embodiment where the access ports include a bellows type of sidewall to further allow for the manipulation of the instruments relative to each other and to the port assembly. In the embodiments where the port assembly is located along the middle section of the port assembly, the hinge or pivot location is located at or below the skin surface of the peritoneum of the patient.

Each of these factors affect the user's ability to manipulate the instrument through the port assembly because an important limitation of the each configuration is the ability to retain the seal between the cavity and the atmosphere. Therefore, as each instrument is manipulated, the surgeon must consider the ability of the port assembly to retain the seal. Furthermore, the ability of the present invention to allow the surgeon to individually manipulate each instrument without compromising the seal is an important consideration. Additionally, the ability to use the present invention with curved instruments provides a major improvement in the ability of the surgeon to reach a desired tissue location without compromising the seal or requiring an additional incision site.

While the preferred forms of the present invention have been particularly shown and described with reference to the preferred embodiments, it will be understood by those skilled in the art that various modifications and changes in form and detail may be made therein without departing from the scope and spirit of the present invention. Accordingly, modifications such as those suggested above, are to be considered to be within and not limited by the scope of the present invention as defined by the following claims.

What is claimed is:

1. A port assembly for temporarily sealing an incision in a patient and formed to enable the introduction of one or more surgical instruments into the body of the patient therethrough while obstructing the flow of gas from a body cavity of the patient to the atmosphere, the port assembly comprising:

a housing having a proximal section and a distal section with a middle section extending therebetween, wherein the housing includes an outer tissue contacting surface and an inner surface forming a cavity therein, and wherein the housing further is a generally conical member and the inner surface is open between the proximal section and distal section;

one or more access ports extending across the cavity of the housing and wherein the one or more access ports form a barrier to the flow of gas therethrough;

a plurality of openings in the one or more access ports wherein the openings are sized to independently receive at least one surgical instrument therethrough and contact the shaft portion thereof; and a plurality of valve members extending across the middle section of the housing that includes the inner surface to selectively obstruct the flow of gas therethrough.

2. A port assembly for temporarily sealing an incision in a patient and formed to enable the introduction of one or more surgical instruments into the body of the patient therethrough while obstructing the flow of gas from a body cavity of the patient to the atmosphere, the port assembly comprising:

a housing having a proximal section and a distal section with a middle section extending therebetween, wherein the housing further includes an outer tissue contacting surface and an inner surface forming a cavity therein;

one or more access ports extending across the cavity of the housing, wherein the one or more access ports form a barrier to the flow of gas therethrough, and wherein the one or more access ports includes at least one valve member wherein the at least one valve member includes at least one flap member obstructing an inner surface opening therethrough and the at least one valve member further includes a lip member extending into the inner surface opening;

a plurality of openings in the one or more access ports wherein the openings are sized to independently receive at least one surgical instrument therethrough and contact the shaft portion thereof; and a plurality of valve members extending across the housing to selectively obstruct the flow of gas therethrough.

3. The port assembly of claim 2 wherein the one or more access ports further include a cap member thereon and the movement of the cap member with respect to the one or more access ports causes the lip member to extend into the inner surface opening and move between first and second positions.

4. A port assembly for temporarily sealing a an incision in a patient and formed to enable the independent introduction of one or more surgical instruments into the body of the patient therethrough while obstructing the flow of gas from a body cavity of the patient to the atmosphere, the port assembly comprising:

a resilient housing having a proximal section and a distal section with a middle section extending therebetween wherein the housing is generally conically shaped and includes an outer tissue contacting surface and an inner surface forming a cavity therein;

a plurality of access ports extending across the cavity of the housing and wherein the access ports form a barrier to the flow of gas therethrough;

an opening in each of the access ports wherein the openings are sized to independently receive at least one surgical instrument therethrough and contact the shaft portion thereof; and a valve member extending across the opening in each of the access ports and the valve member includes at least one flap member to obstruct the flow of gas from the body cavity of a patient to the atmosphere and the valve member further including a lip member thereon and the lip member is sized to engage the shaft of an instrument in at least one position thereof.

* * * * *